(12) United States Patent
Pindl et al.

(10) Patent No.: US 11,926,521 B2
(45) Date of Patent: Mar. 12, 2024

(54) IR EMITTER WITH GLASS LID

(71) Applicant: Infineon Technologies AG, Neubiberg (DE)

(72) Inventors: Stephan Pindl, Ergoldsbach (DE); Carsten Ahrens, Regensburg (DE); Stefan Jost, Munich (DE); Ulrich Krumbein, Rosenheim (DE); Matthias Reinwald, Laaber (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 519 days.

(21) Appl. No.: 17/150,527

(22) Filed: Jan. 15, 2021

(65) Prior Publication Data

US 2021/0246016 A1 Aug. 12, 2021

(30) Foreign Application Priority Data

Feb. 7, 2020 (EP) .................................. 20156205

(51) Int. Cl.
*B81B 7/00* (2006.01)
*B81C 1/00* (2006.01)
*G01N 29/24* (2006.01)
*G01N 33/00* (2006.01)

(52) U.S. Cl.
CPC ........ *B81B 7/0067* (2013.01); *B81C 1/00317* (2013.01); *G01N 29/2418* (2013.01); *G01N 33/0027* (2013.01); *B81B 2201/0214* (2013.01); *B81B 2203/0127* (2013.01); *B81B 2207/095* (2013.01)

(58) Field of Classification Search
CPC ....... G01N 2021/1704; G01N 29/2418; G01N 33/0027
See application file for complete search history.

(56) References Cited

U.S. PATENT DOCUMENTS

| | | | |
|---|---|---|---|
| 8,575,578 B1* | 11/2013 | Shie | G01N 21/3504 250/496.1 |
| 10,681,777 B2* | 6/2020 | Kautzsch | G01N 29/02 |
| 10,955,599 B2* | 3/2021 | Pindl | G02B 5/281 |
| 11,609,180 B2* | 3/2023 | Qi | B81B 7/0067 |
| 2016/0308084 A1* | 10/2016 | Bieselt | G01J 3/108 |
| 2017/0012199 A1* | 1/2017 | Sabry | G01J 3/0208 |
| 2017/0290097 A1 | 10/2017 | Pindl et al. | |
| 2018/0146512 A1* | 5/2018 | Pindl | G02B 5/208 |
| 2019/0148101 A1 | 5/2019 | Eberl et al. | |
| 2021/0055207 A1* | 2/2021 | Mittereder | G01N 21/1702 |

FOREIGN PATENT DOCUMENTS

| | | | | |
|---|---|---|---|---|
| CN | 107265392 B | * | 6/2020 | ............. B81B 7/00 |
| DE | 102017126635 A1 | * | 5/2019 | ............. H01J 19/54 |
| JP | 2019528558 A | * | 10/2019 | |
| WO | WO-2020043709 A1 | * | 3/2020 | ........... A61B 1/0684 |

* cited by examiner

*Primary Examiner* — Andre J Allen
(74) *Attorney, Agent, or Firm* — Slater Matsil, LLP

(57) ABSTRACT

An infrared emitter with a glass lid for emitting infrared radiation comprises a package enclosing a cavity, wherein a first part is transparent for infrared radiation and a second part comprises a glass material and a heating structure configured for emitting the infrared radiation, wherein the heating structure is arranged in the cavity between the first part and the second part of the package.

20 Claims, 9 Drawing Sheets

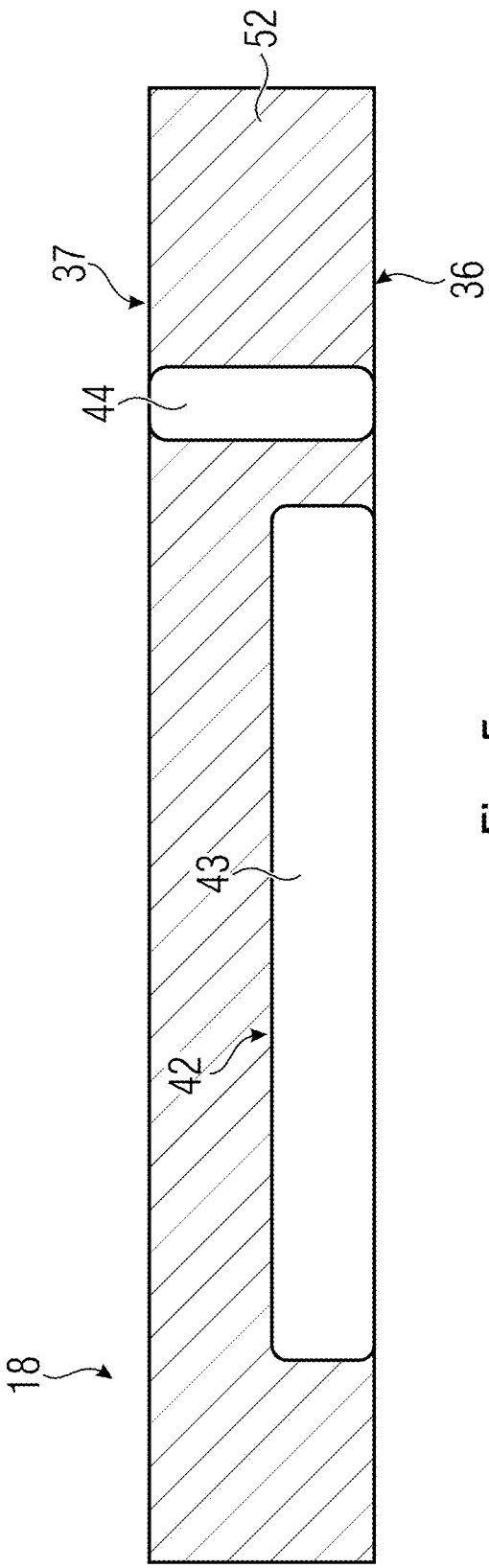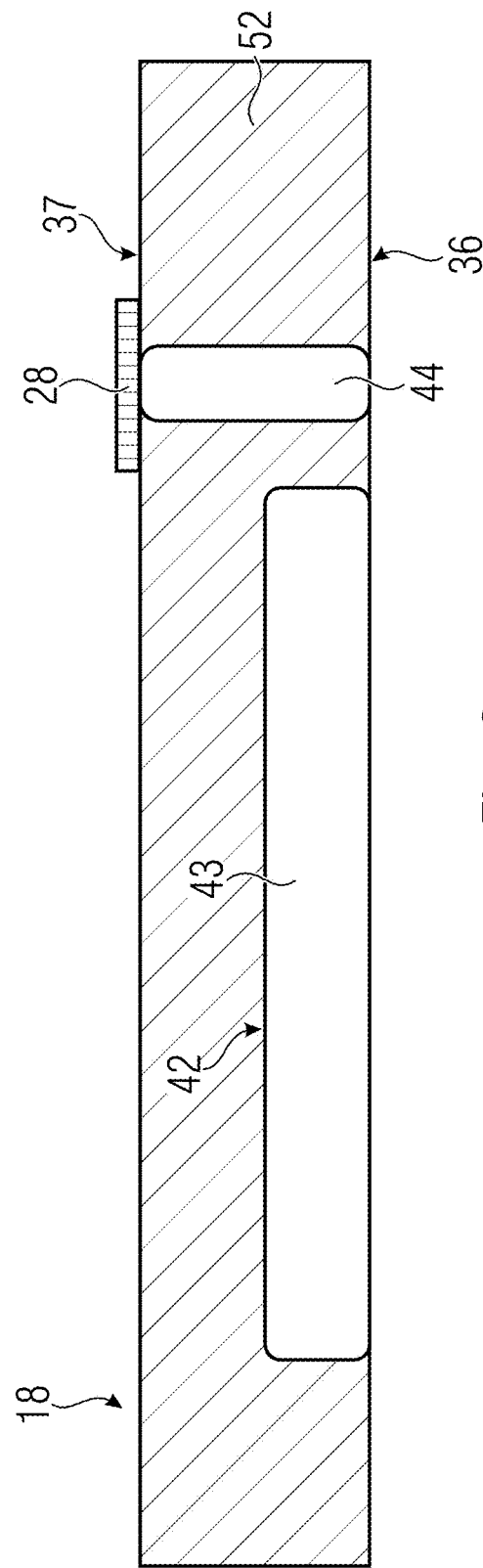
Fig. 5
Fig. 6

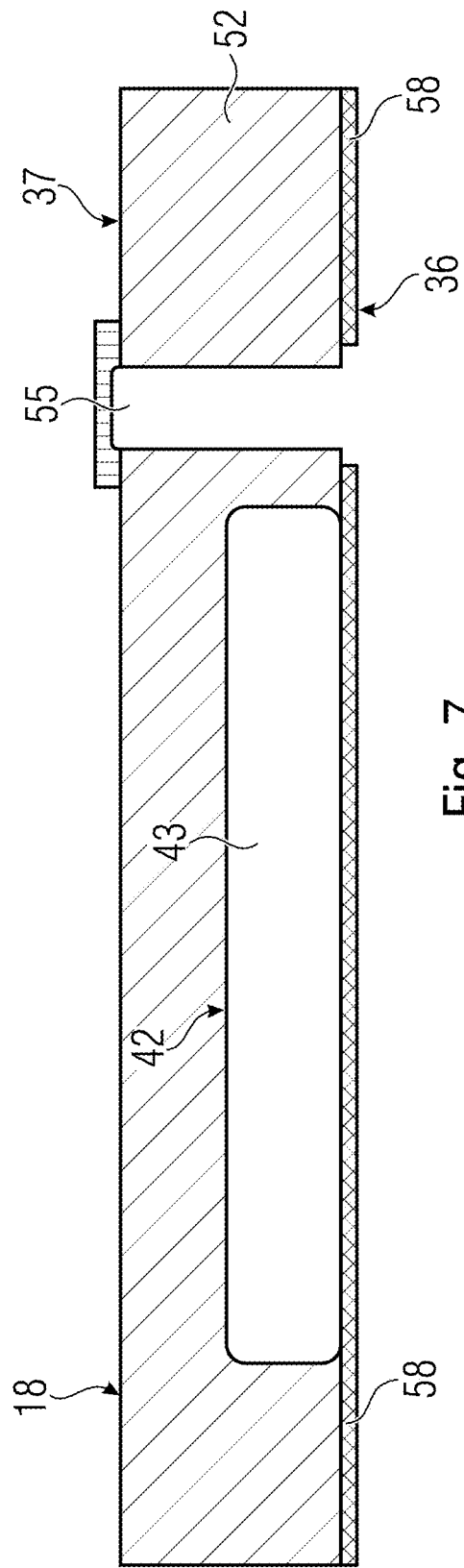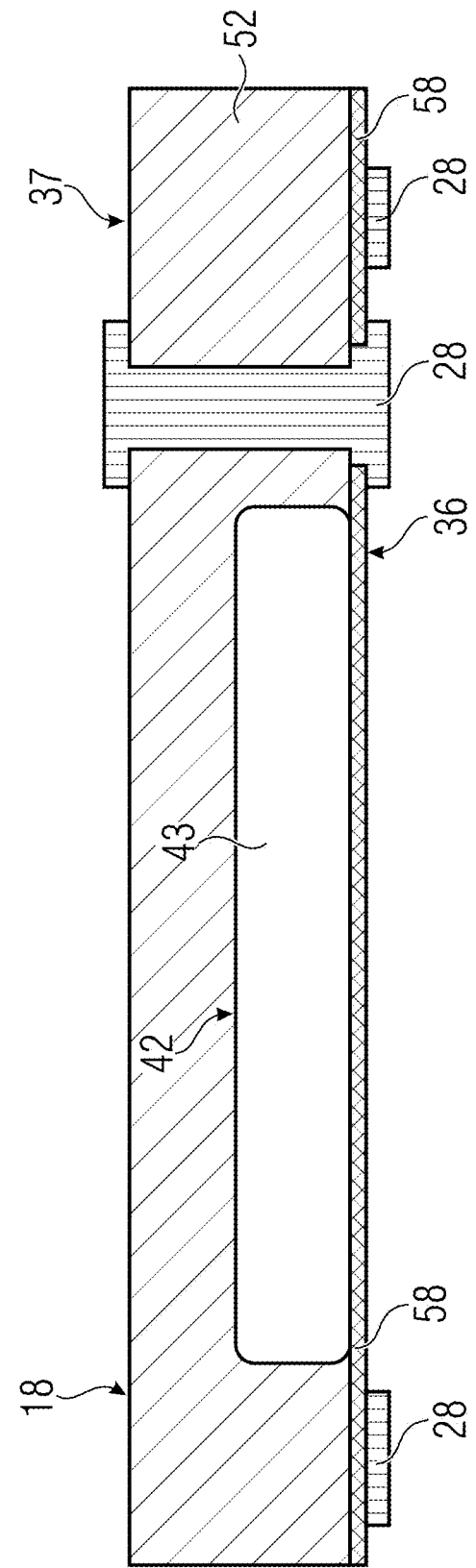

IR EMITTER WITH GLASS LID

This application claims the benefit of European Patent Application No. 20156205.5, filed on Feb. 7, 2020, which application is hereby incorporated herein by reference.

TECHNICAL FIELD

Embodiments of the present disclosure relate to an emitter, for example, an infrared source combined with a glass lid.

BACKGROUND

The sensing of environmental parameters, such as noise, sound, temperature and gases gains more and more importance within mobile devices, home automation and the automotive sector. Harmful gas concentrations can occur due to pollution and malfunction of certain devices. The well-being is strongly influenced by the air quality. Gas detection by cheap, always available and connected sensors is an upcoming topic in the future.

For integrated circuits like MEMS the size and height may be an aspect to be considered—especially if the chip should be implemented in mobile devices like a smartphone. Additionally, the costs may be considered for MEMS solutions.

Thus, it is desired to provide an IR emitter, in which the emitter filter package is reduced in size, height, robust, reliable and at the same time producible at low cost.

SUMMARY

According to an embodiment an emitter may comprise a package enclosing a cavity, wherein a first part of the package may be transparent for infrared radiation, i.e., the silicon substrate, and a second part of the package may comprise a glass material, i.e., the opaque substrate or the non-transparent substrate. The emitter may further comprise a heating structure, i.e., the IR emitter configured for emitting the infrared radiation, wherein the heating structure may be arranged in the cavity between the first part of the package and the second part of the package.

According to a further embodiment a method for manufacturing an emitter may comprise providing a heating structure; providing a first part of a package being transparent for infrared radiation; and a second part of the package comprising a glass material; such that the heating structure is arranged in a cavity enclosed by the package between the first part of the package and the second part of the package; such that the heating structure is configured for emitting the infrared radiation.

Further embodiments are described in the dependent claims.

BRIEF DESCRIPTION OF THE DRAWINGS

In the following, embodiments of the present disclosure are described in more detail with reference to the figures in which:

FIG. 5 shows a schematic cross-sectional view of a thinned glass layer;

FIG. 6 shows a schematic cross-sectional view of a glass layer with metallization;

FIG. 7 shows a schematic cross-sectional view of a glass layer with a masking and wet etch of a through glass via (TGV);

FIG. 8 shows a schematic cross-sectional view of a glass layer with a through glass via (TGV) and metallization;

DETAILED DESCRIPTION OF ILLUSTRATIVE EMBODIMENTS

Figure 1:
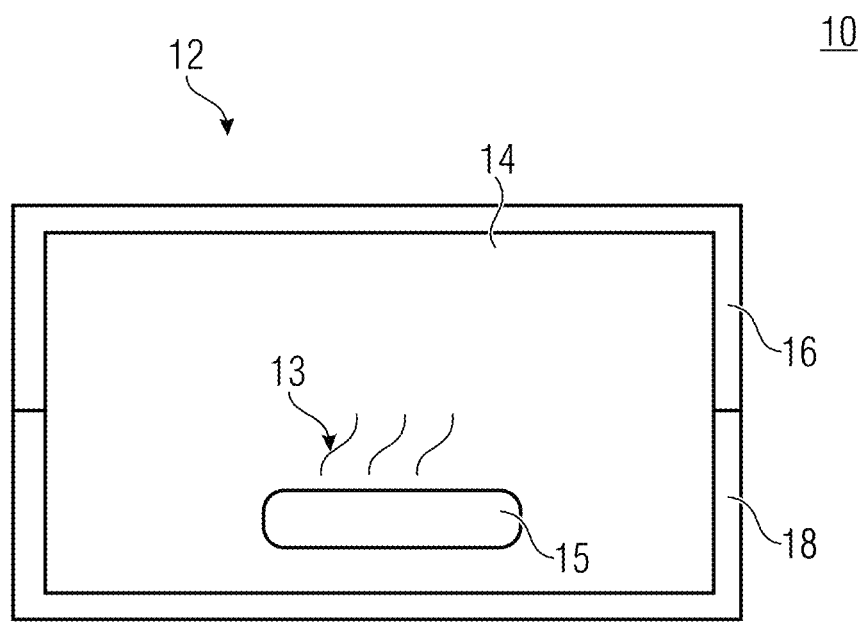
FIG. 1 shows a schematic cross-sectional view of a two-part package enclosing a cavity according to an embodiment.

In the following description, a package is a housing for electronic systems or electronic devices, for example, semiconductor devices, printed circuit boards (PCB), integrated circuits (IC) and thick-film devices, for enclosing or protection from mechanical damage, cooling, radio frequency, noise, emission and electrostatic discharge. Product safety standards may influence or dictate particular features of a consumer product, for example, external case temperature or grounding of exposed metal parts. Prototypes and industrial equipment made in small quantities may use standardized commercially available enclosures such as card cages or prefabricated boxes. Mass-market consumer devices may have highly specialized packaging to increase consumer appeal.

Many electrical products require the manufacturing of high-volume, low-cost parts such as enclosures or covers by techniques such as injection molding, die casting and investment casting. The design of these products depends on the production method and require careful consideration of dimensions and tolerances and tooling design. Some parts may be manufactured by specialized processes such as plaster-, sand-casting of metal enclosures, wafer level processes or wafer-to-wafer bond processes, which is explained more detailed in this enclosure.

In the design of electronic products, it is crucial to perform analyses to estimate such things as maximum temperatures for components, structural resonant frequencies, and dynamic stresses and deflections under worst-case environments. Such knowledge is important to prevent immediate or premature electronic product failures.

Before discussing the present embodiments in further detail using the drawings, it is pointed out that in the figures and the specification identical elements and elements having the same functionality and/or the same technical or physical effect are usually provided with the same reference numbers or are identified with the same name, so that the description of these elements and of the functionality thereof as illustrated in the different embodiments are mutually exchangeable or may be applied to one another in the different embodiments. In the following description, a plurality of details is set forth to provide a more thorough explanation of embodiments. However, it will be apparent to those skilled in the art that embodiments may be practiced without these specific details. In addition, features of the different embodiments described hereinafter may be combined with each other, unless specifically noted otherwise. The specific embodiments discussed are merely illustrative of specific ways to make and use the present concept, and do not limit the scope of the embodiments.

It is possible to place an IR emitter and a filter as separate devices and separately in a common package. For example, the filter may be directly placed on the emitter, but it is also possible to place them chip on chip. This solution may occupy much space, for example on a chip, a PCB (Printed Circuit Board) or a wafer. For some applications, such solutions may be too big in height and size and therefore not useful, e.g., in mobile devices. Some embodiments, thus, relate to an IR emitter and an IR filter which may be implemented in a single package, e.g., together with additional other chips on a PCB or wafer.

It is understood that when an element is referred to as being "connected" or "coupled" to another element, it may be directly connected or coupled to the other element, or intermediate elements may be present. Conversely, when an element is referred to as being "directly" connected to another element, "connected" or "coupled," there are no intermediate elements. Other terms used to describe the relationship between elements should be construed in a similar fashion (e.g., "between" versus "directly between", "adjacent" versus "directly adjacent", and "on" versus "directly on", etc.).

Embodiments described herein may relate to an emitter. Such emitters may be configured for emitting an electromagnetic radiation which may comprise a certain wavelength range. Such an electromagnetic radiation may be used in connection with further structures amongst which sensors form embodiments of the present disclosure. By way of non-limiting example only, such emitters may be used for sensor applications such as photoacoustic gas sensors that use the electromagnetic radiation for exciting gas molecules so as to allow for determining a presence and/or a concentration of one or more types of gasses based on the generated excitation. Such sensors may be operated, for example, by use of electromagnetic radiation that comprises at least a part of an infrared (IR) spectrum. For limiting the emitted spectrum, the emitter may be adapted in view of generating the electromagnetic radiation in the desired wavelength spectrum and/or may comprise or may be combined with a filter structure that allows to exclude or damp undesired wavelength ranges.

Although embodiments are described in connection with IR emitters, the disclosure is not limited hereto. That is, embodiments may also relate to different wavelength ranges.

FIG. 1 shows a schematic cross-sectional view of an emitter 10 according to an embodiment. According to an embodiment, the emitter 10 may be a micro electromechanical system (MEMS). The emitter 10 may comprise a package 12 enclosing a cavity 14. The package 12 may comprise a first part 16 of the package 12 transparent for at least a part of a radiation that may be understood as infrared radiation 13. The infrared radiation 13 may comprise a wavelength range of, e.g., between 0.7 µm and 30 µm. The emitted wavelength radiation 13 may comprise at least a part of thereof, not excluding thereby to emit additional wavelengths, e.g., below 0.7 µm or above 30 µm. In connection with the present embodiments, the radiation 13 emitted may be considered as radiation having a desired wavelength range from the possibly larger wavelength range being generated.

Being transparent may be understood as allowing an amount of at least 50%, at least 70% or at least 90%, e.g., 95% to travel through the material, at least for the desired wavelength range. By way of example, semiconductor materials may be transparent for infrared radiation 13. Further, the package 12 may comprise a second part 18 of the package 12, which comprises a glass material.

That is, the first part 16 of the package 12 may comprise a semiconductor material, for example, comprising a silicon material a gallium-arsenide material and/or a different semiconductor substrate material. The semiconductor material may be a doped or undoped semiconductor material. Alternatively, or in addition, the first part 16 may comprise a metal material comprising one or more metal materials, the metal material, the obtained combination or alloy respectively, being transparent for the desired part infrared radiation 13. The first part 16 of the package 12 may comprise a filter structure 25 transparent for infrared radiation 13. Alternatively, the filter structure 25 may be arranged at a different position or the emitter 10 may be implemented without the filter structure 25.

Figure 12:
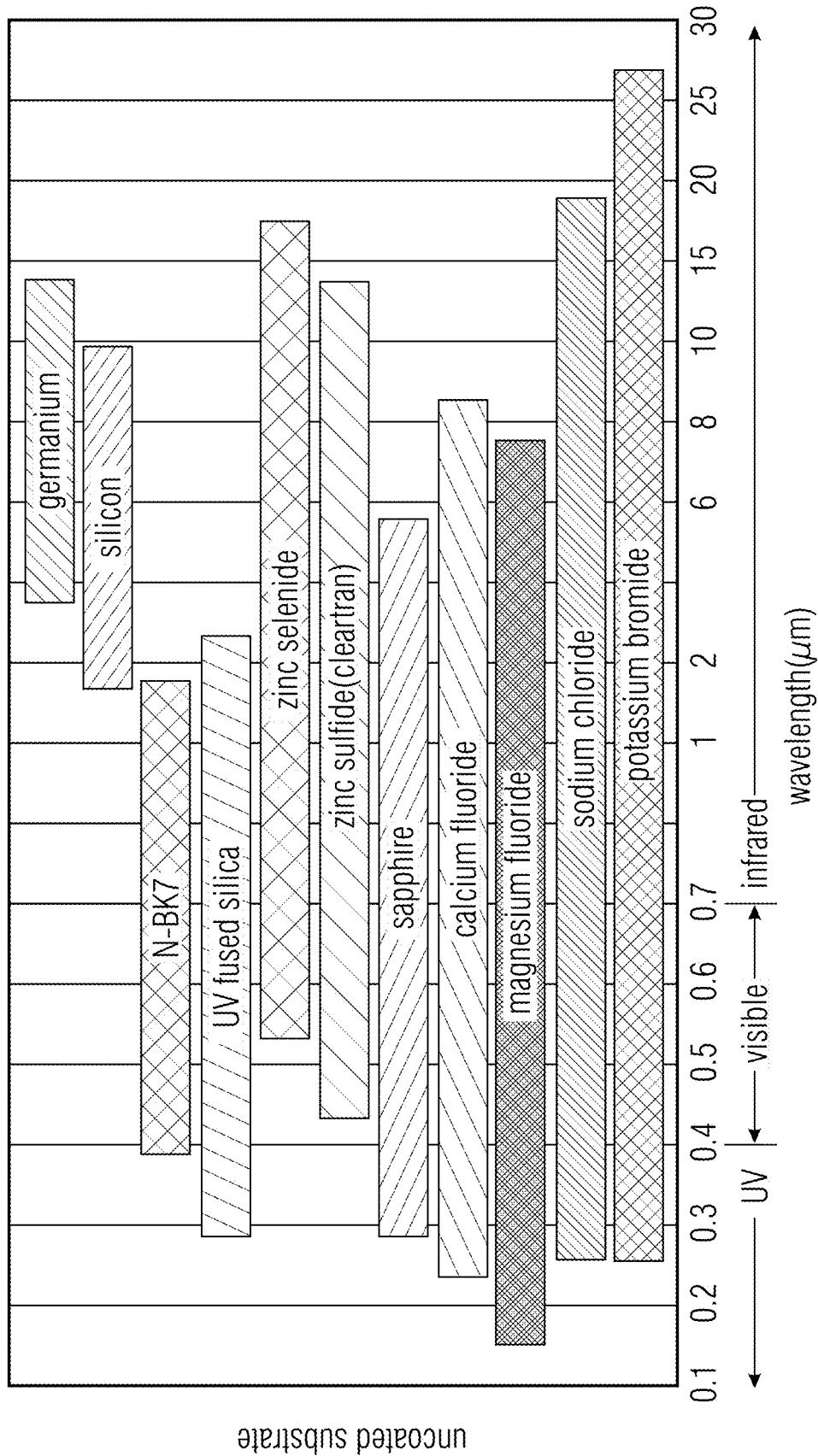
FIG. 12 shows a substrate-wavelength-diagram.

The second part 18 of the package 12 may comprise a glass material. In this description, the glass material may be referred to as the glass substrate 32. The glass substrate 32 may be obtained in thin structures whilst providing for a high robustness. Additionally, a topology of the glass structure may be generated with high precision, thus allowing to obtain high quality emitters. The glass substrate 32 may be at least in parts non-transparent or even opaque or act as a damping structure for at least parts of the infrared radiation 13 for which the first part 16 is transparent. This may allow to implement a directivity structure, i.e., to provide for an aperture structure within the emitter 10 by the material selected for the second part 18 of the package 12, whilst avoiding additional elements and whilst making use of the other advantages provided. The glass substrate 32 may comprise a material such as N-BK7 which is shown in FIG. 12. The wavelength range for N-NBK7 is representative for the majority of materials used for visible wavelengths such as B270, N-SF11 or BORAFLOAT®.

The heating structure 15 may be configured for emitting infrared radiation 13 that comprises an infrared wavelength range from between 0.7 µm and 30 µm. The heating structure 15 is arranged in the cavity 14 between the first part 16 of the package 12 and the second part 18 of the package 12. That is, the package 12 may house the heating structure 15.

An aspect of the present disclosure concerns a gas sensor being or comprising, inter alia, a photoacoustic sensor comprising the IR emitter 10 in the cavity 14. The photoacoustic sensor may be configured to detect a gas in an environment according to the photoacoustic principle. Accordingly, the emitter 10 may be configured to emit IR radiation 13, in a predetermined wavelength spectrum into a measurement cavity. The particular wavelength of the emitted IR radiation 13 may be selected based on the gas to be detected, i.e., the so-called target gas. The emitter 10 may be configured to intermittently emit the IR radiation 13. During operation, the environmental gas inside the measurement cavity, including the target gas, may absorb the emitted radiation 13 and, in consequence, the gas may intermittently heat up and cool down in reaction to the intermittently emitted IR radiation 13. This intermittent absorption and related heating and cooling of the gases inside the measurement cavity may produce an alternating increase and decrease of pressure inside the measurement cavity. These pressure variations may be detected by an acoustic transducer, for example, a MEMS microphone or MEMS structures that implement a membrane hinged vibratable and connected to the excited gases.

The amount of absorption of the emitted IR radiation 13 by the gases and the related pressure variations inside the measurement cavity may depend on the sort of gas inside the measurement cavity and it may vary with the respective target gas. Each target gas may comprise a characteristic absorption spectrum, i.e., it may cause characteristic pressure variations in response to the intermittently emitted IR radiation 13. Said characteristic absorption spectrum may also be referred to as a gas-specific fingerprint. Accordingly, the acoustic transducer may record a signal that may be characteristic for the respective target gas, such that a signal generated by the acoustic transducer may thereby form a basis to detect and identify the respective target gas, e.g., by use of a circuitry being adapted accordingly.

For example, a central processing unit (CPU) an integrated circuit (IC) an application specific integrated circuit (ASIC), a microcontroller or a field programmable gate array (FPGA) may be connected to the acoustic transducer and possibly to the emitter 10 to allow for a good synchronization.

Figure 2:
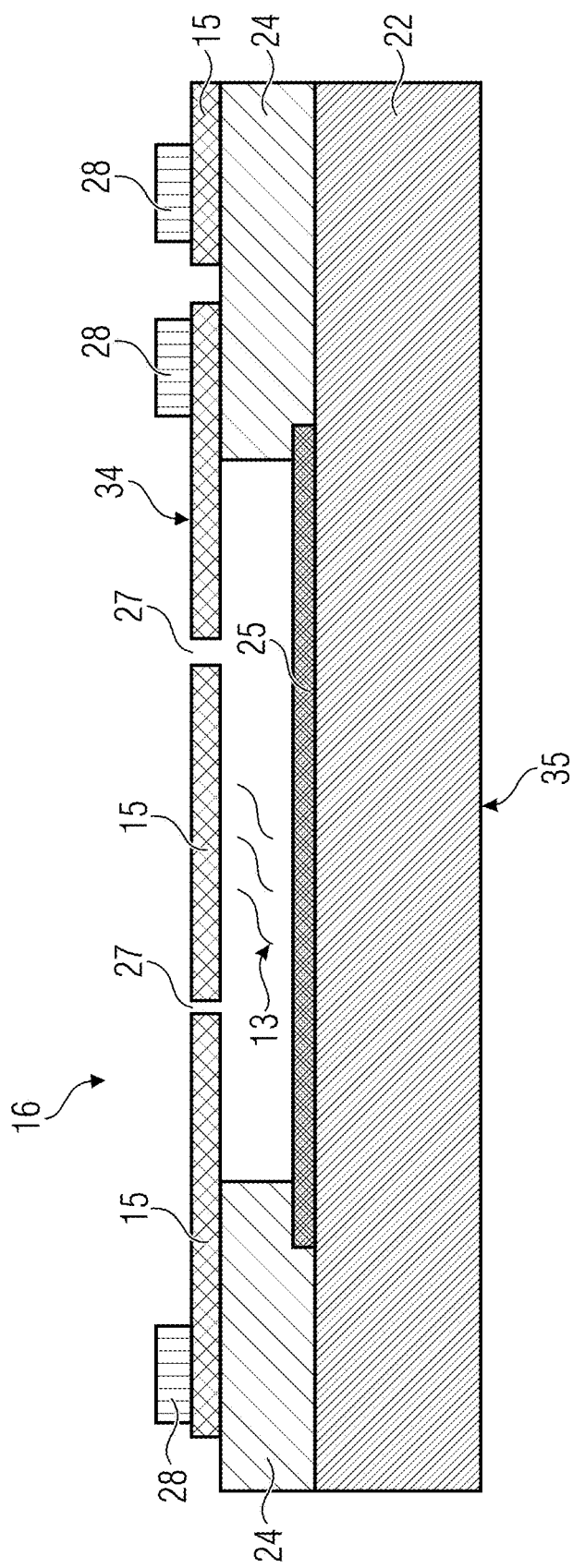
FIG. 2 shows a schematic cross-sectional view of a first part of the package with typical IR emitter structure with filter layers.

FIG. 2 shows a schematic cross-sectional view of an implementation of the first part 16 of the package 12 according to an embodiment. The first part 16 may be implemented or may comprise a plurality of layers. The first part 16 may comprise the heating structure 15, a semiconductor substrate 22, a spacer layer 24 between the semiconductor substrate 22 and the heating structure 15, a filter structure 25, and a metallization structure 28. The semiconductor substrate 22 may comprise one or more semiconductor materials, for example, silicon, gallium arsenide, gallium nitride and/or silicon carbonite.

The substrate 22 may comprise a first and an opposing second main side. The first main side and/or the second main side may be parallel to a x/y plane based on an x direction and a perpendicular y-direction, wherein a z-direction may be perpendicular to both, the x-direction and the y-direction. The z-direction may be referred to as a depth-direction, wherein depth shall not be understood as limiting the examples described herein to a specific direction in space.

The spacer layer 24 may comprise for example, electrically insulating material such as SiO2 and/or SiN. The spacer layer 24 may comprise at least one layer for retaining a distance, e.g., space or gap, arranged between the semiconductor substrate 22 and the heating structure 15. For example, a space between the layers can be selected within a broad range, e.g., based on the other geometries of the device or the application. By way of non-limiting example, the space layer 24 may cover a distance between 100 nm up to 10 μm.

The first part 16 of the package 12 may be part of the emitter 10. For example, the first part 16 and the second part 18 may form a stack, e.g., in an arrangement on top of each other, one superimposed on the other or stacked on top of each other. The cavity 14 may be housed or sealed between the first part 16 and the second part 18. That is, the first part 16 of the package 12 may form a component of an emitter 10 but may be implemented separately or individually. To form the emitter 10, the filter structure 25 may comprise, for example, an infrared filter, an infrared filter stack or a filter chip and may be configured to selectively transmit at least a part of the IR radiation 13, e.g., in a predetermined wavelength range.

According to an embodiment, the filter structure 25 may comprise monotonically integrated filter layers. The filter structure 25, for example, may comprise one or a plurality of layers commonly providing for a filter characteristic so as to transmit a predetermined wavelength range, e.g. at least a part of an infrared wavelength range or a different part of an infrared wavelength range. For example, the predetermined wavelength range may comprise a wavelength between 0.7 μm and 30 μm, 0.9 μm and 20 μm or between 1 μm and 10 μm. The wavelength range may be adapted according to the target gas of a later sensor, encapsulated from the measurement cavity of the photoacoustic sensor. For example, the measurement cavity may relate to the photoacoustic sensor containing the target gas, while the cavity 14 relates to the emitter in which the package 12 encloses the cavity 14.

According to an embodiment, the filter structure 25 may comprise a stack having one or more layers configured for filtering the IR radiation 13, e.g., in a predetermined wavelength range. Thereby, the at least one layer may provide for filtering the infrared radiation 13 so as to let pass the predetermined wavelength range. Optionally, the stack of layers may comprise a variation of at least one property between layers. The variation may be implemented regularly or irregularly and may, wherein some embodiments provide for layers that comprise a periodic variation of the at least one property. An example property may be a height, depth or width of the layer whilst having a same or a varying layer material.

For example, the filter structure 25 may comprise at least two layers having the same or different materials. According to an embodiment, the filter structure 25 may be arranged on a surface of the semiconductor substrate 22.

According to an embodiment, the filter structure 25 may be configured to at least partially reflect a range of infrared wavelength which may be impractical for gas sensing, such as a Bragg reflector. By reflecting the part of the wavelength portion that is possibly unwanted whilst transmitting other wavelength rages, a filtering with regard to the transmission direction through the filter structure 25 may be implemented.

According to an embodiment, the heating structure 15 may comprise an element to generate heat, thereby providing for a source of infrared radiation. Such an element may be operated by electric power, wherein electric losses may provide for generation of the heat. Whilst any possible source for infrared radiation may be used, arranging a membrane structure may allow to obtain the radiation efficiently and in a large area. The membrane structure may comprise one or more ventilation holes 27 like in acoustical membranes or diaphragms. The membrane structure may be arranged at and/or on the surface of the heating structure 15 having ventilation holes 27 forming a path from the first side 34 of the first part 16 of the package 12 to the filter structure 25. The heating structure 15 configured for emitting an infrared radiation 13 may excite a movement of the membrane structure based on an asymmetric energy absorption of the infrared radiation in the first part 16 and the second part 18. An example for such a membrane structure may be a circular structure, e.g., a round or circular membrane, or a quadratic membrane structure. Such a membrane structure may be formed, for example, similar to a membrane structure being used in MEMS microphones or MEMS loudspeakers.

The heating structure 15 may comprise a metallization structure 28 being electrically conductive and which is configured for generating IR radiation 13 responsive to an electrical current, for example copper, gold, silver, platinum or the like, configured as a part of a metal—semiconductor junction. According to an embodiment the metallization structure 28 may comprise a pad or multiple pads coupled directly on the heating structure 15 providing electric connectivity for the heating structure 15 so as to emit the infrared radiation 13. Further, the shape may include a ring, square or circular shape. In addition, the metallization structure 28 coupling the heating structure 15 of the first part 16 of the package 12 with the metallization structure 28 of the second part 18 being arranged on the surface of the heating structure 15 facing the first side 34 of the first part 16 of the package 12 so as to the ventilation holes 27 remain uncovered.

The heating structure 15 may be arranged on a surface of the first part 16. The surface of the first part 16 may be referred to as a first side 34 of the first part 16. A side of the first part 16 that opposes the first side 34 may be referred to as a second side 35 of the first part 16. Thus, the semiconductor substrate 22 may be arranged on the second side 35 of the first part 16. The heating structure 15 may be spaced from the semiconductor substrate by the spacer layer 24.

Figure 3:
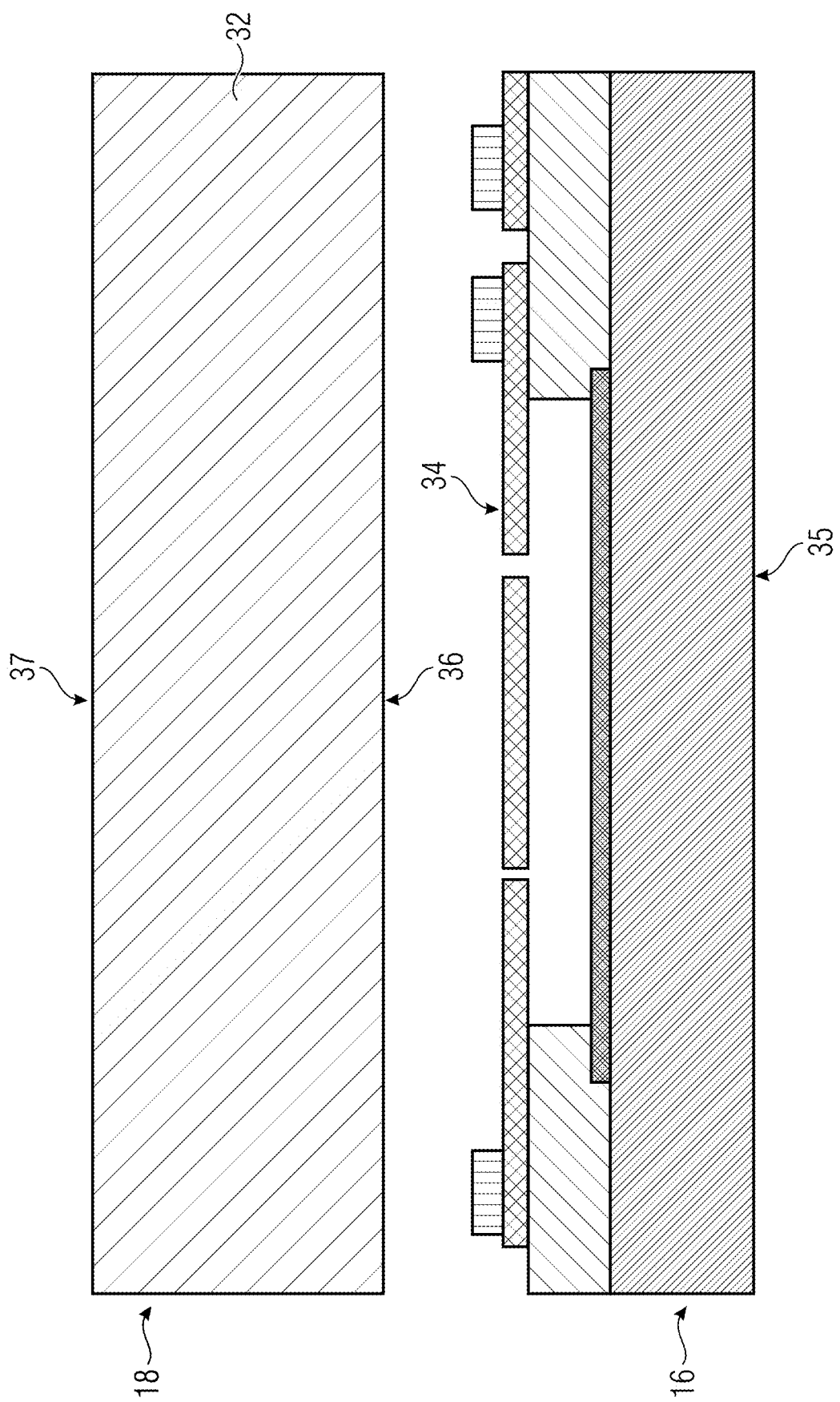
FIG. 3 shows a schematic cross-sectional view of a first part of the package with typical IR emitter structure with filter layers and a glass layer.

FIG. 3 shows a schematic cross-sectional view of the first part 16 of the package 12 as shown in FIG. 2 and the second part 18 of the package 12 which comprises a glass substrate 32. The first part 16 of the package 12 may be transparent for the predetermined wavelength range in a first amount. The second part 18 may also be transparent for the predetermined wavelength but in a second amount that is lower compared to the first amount. Alternatively, the second part 18 may be opaque for the predetermined wavelength range.

To form the second part 18 from the glass substrate, embodiments comprise forming at least one recess 53 in the glass substrate 32. The at least one recess 53 may be understood as a pocket or an opening extending through a part or an overall thickness of the glass material. Different recesses 53 may be formed equal or different with regard to a depth or lateral extension. For generating the at least one recess 53, embodiments comprise execution of a subtractive or/and an additive process such as material etching, material cutting, material jetting, material extrusion and/or polymerization. By way of example, one possible process is described in FIG. 4. In a later emitter 10 the heating structure 15 may be arranged between the filter structure 25 and the second part 18. This allows the IR radiation 13 to travel through the semiconductive substrate 22 filtered, whilst being possibly damped by the second part 18. The surface of the glass substrate 32 which faces the first side 34 of the first part 16 may be referred to as the first side 36. Thus, the side that opposes the first side 36 of the second part 18 may be referred to as the second side 37 of the second part 18.

Figure 4:
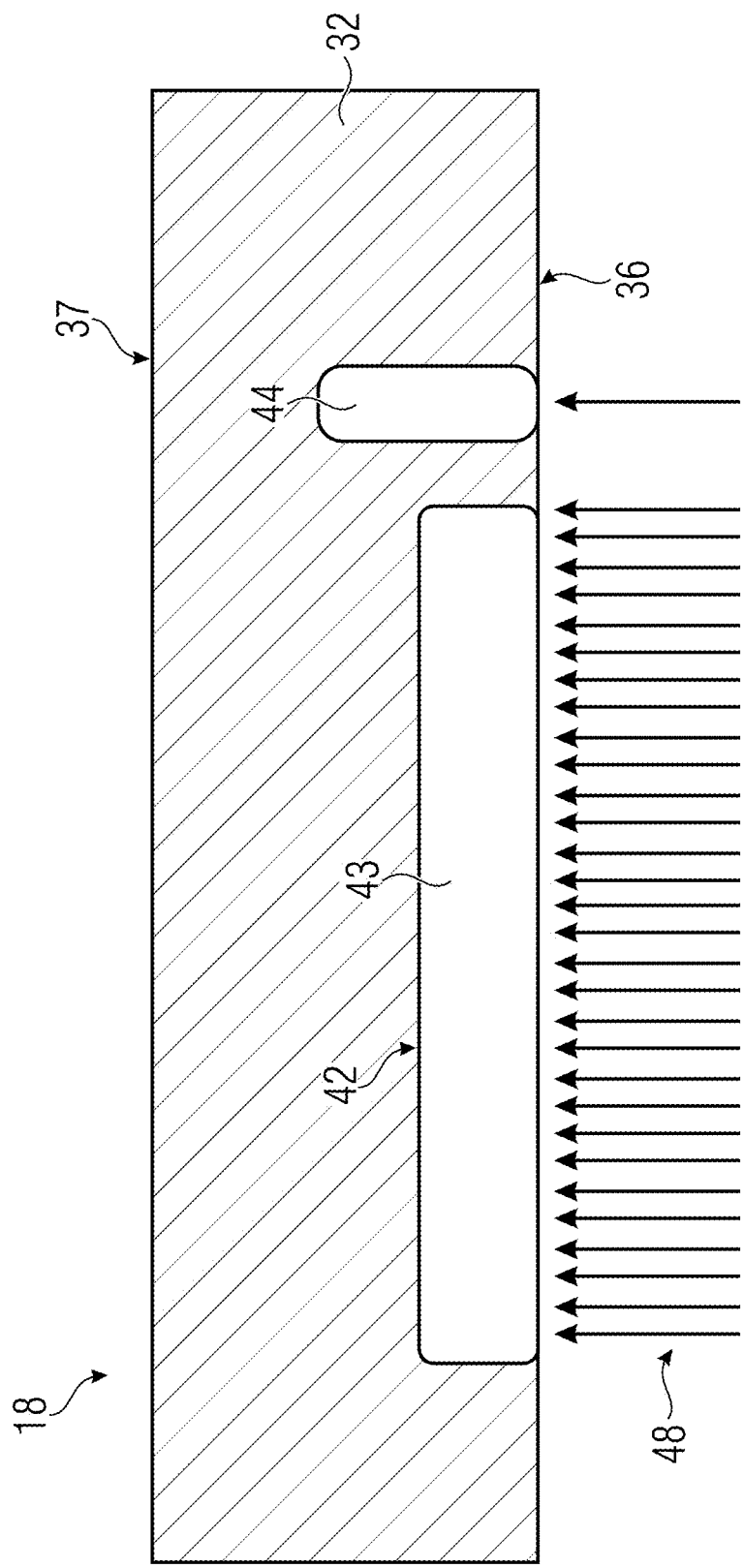
FIG. 4 shows a laser induced glass damage.

FIG. 4 shows a schematic side view of a glass substrate 32 from which the second part 18 of an emitter 10 that is in accordance with present embodiments may be obtained. At least one laser beam 48 may be used to damage the glass substrate 32 in a recess region in which a later recess 53 is aimed to be obtained. The recess 53 may form a hollow in the glass substrate 32 so as to partly reduce the thickness thereof to a non-zero value. Alternatively, in the recess 53 may reduce the thickness to a zero-value thereby providing for a via-opening in the glass substrate 32. For example, a focus of the at least one laser beam 48 may be variably set to a varying point of the glass substrate 32 to change the structure of the glass substrate 32 at this point responsive to the absorbed energy provided by that at least one laser beam 48. The changed structure of the glass may, for example, feature a glass substrate 32 damaged 43, and/or deeper damaged 44, and/or thinned 52. The difference of a damaged glass substrate 43 and a deeper damaged glass substrate 44 may occur in difference width and/or depth of at least one recess region, when compared to each other.

The changed structure may allow for an easy and precise etching of the damaged glass substrate region 43 so as to obtain the recess 53. Such a process may allow for easy and precise definition of depths along z and/or lateral extensions along x and/or y of recesses 53. In particular, embodiments allow to obtain a high aspect ratio, i.e., a large value of a depth along z compared to a lateral extension along x and/or y.

For example, in a group of recesses 53 that all have an aspect ratio of 1:5, one recess 53 might be 1 mm wide and 5 mm deep, another 1 µm wide and 5 µm deep, and a third might be 2 µm wide and 10 µm deep. Thus, the aspect ratio concerns the relationship of the width to the depth, not a recess's actual size. Such a process further allows to obtain high aspect ratios although the process is not limited to such aspect ratios. For example, the aspect ratio being based on a depth of the recess 53 being compared to a shortest lateral extension along x or z according to width (shortest lateral extension)/depth (vertical extension) may be at least 1:5, 1:7, 1:10 or even more. Using damaged glass may result in high aspect ratio structures parallel to each other.

The at least one laser beam 48 may allow to create structures or damaged regions smaller than 5 µm of a lateral extension along x/y. The laser being configured for adjusting the intensity of the laser beams 48 such that the glass substrate 32 is damaged to a predefined width and depth resulting in the so-called damaged glass substrate region 43. For example, the damaged glass substrate region 43 may ease a removal process, e.g., wet etching, dry etching, wafer cleaning and polymer removal. To obtain such a high-aspect ratio in the range of at least bigger than 1:10 in the glass substrate 32 a laser-inducted deep etching (LIDE) may be performed. For example, the high-aspect ratio may be in a range between 1:10 and at most 1:50, e.g., a normalized width of 1 and a compared depth of 10 times the width. In a step of generating the recess 53, the glass substrate 32 may be locally modified, for example, on the first side 34 of the glass substrate 32 by laser pulses according to the desired layout, for example, the damaged glass substrate region 43. A single laser pulse may suffice to modify the glass substrate 32 through their entire thickness.

Masked isotropic wet etching of glass is hardly capable to produce micro-features of aspect ratios larger than one. Standard laser drilling of glasses is typically associated with low throughput and hidden micro-cracks and thermal induced stress which can lead to yield loss and or catastrophic failures of the final device. In contrast to conventionally drilled micro holes, through glass vias 55 made by laser-induced deep etching (LIDE) are free of micro cracks, chipping, thermal stress. The side walls of LIDE-generated micro-holes are smooth, crack-free, chip-free, and stress-free, enabling reliable metallization. The taper angle may range between 0.1° and 30°.

The damaged glass substrate region 43 may later, for example, after the wet etching or the deep etching, result in a recess 53 at the first side 36 of the second part 18. According to an embodiment, the damaged glass substrate region 43 may comprise a predetermined height, width and depth ratio in a first amount and a variety of different height, width and depth ratio in a second amount, for example, the deeper damaged glass substrate region 44 resulting in a variety of damaged glass regions 43 in the glass substrate 32. According to an embodiment, the variety of height, width and depth ratio in a second amount may be, for example, a deeper damaged glass substrate region 44 than the damaged glass substrate region 43. Further, the deeper damaged glass substrate region 44 may provide a foundation for a resulting trough glass via 55 (TGV) shown in FIG. 7.

According to an embodiment, the glass substrate 32 may comprise a variety of damaged glass substrate regions 43 and/or a variety of deeper damaged glass substrate regions 44 arranged as a parallel structure so as to face the first side 36 of the second part 18. According to an embodiment, the damaged glass substrate regions 43 may comprise the deeper damaged glass substrate regions 44, but not vice versa.

FIG. 5 shows a schematic cross-sectional view of the glass substrate 32 with an at least one recess region 42 and the damaged glass substrate region 43 after a performed thinning process. After performing a removing material process, e.g. thinning, on the structure of the glass substrate 32 of FIG. 4, the structure of the glass substrate 32 of FIG. 5 may be obtained. The thinning process may comprise a laser-cutting process, a knife-cutting process, machining, performing a cutting or a material chemical reaction that results in thickness reduced glass substrate 32. The in thickness reduced glass substrate 32 may be referred to as thinned glass substrate 52. Alternatively or in addition, a removing material process may be performed on the semiconductor substrate 22, and/or the filter structure 25 and/or the spacer layer 24 so as to obtain the desired thickness.

That is, after performing the thinning process on the second side 37 the deeper damaged glass substrate region 44 may result in a glass substrate 32 with a damage through their entire thickness and later in a through glass via 55. In other words, the deeper damaged glass substrate region 44 from FIG. 4 is now a glass substrate 32 having a damage through their entire thickness reaching from the first side 36 of the second part 18 to the second side 37 of the second part 18. Although the glass substrate 32 is described as remaining unchanged on the first side 36, optionally process steps may be carried out that modify the glass substrate 32 on the first side 36, e.g., arranging or removing materials.

FIG. 6 shows a schematic cross-sectional view of the thinned glass substrate 52 with an added metallization structure 28 such as the metallization structure 28 already shown in FIG. 2. The metallization structure 28 may comprise a connection material or a connection layer which may provide an electrical link resulting in a later connection from the second side 37 of the second part 18 to the first side 36 of the second part 18. The metallization structure 28 may be arranged directly on, at or in the later obtained through glass via 55, for example, such as a lid, cap or cover providing electric conductivity. The thinned glass substrate 52 may still remain unchanged on the first side 36 of the second part 18.

FIG. 7 shows a schematic cross-sectional view of the thinned glass substrate 52 with a masking layer 58 on the first side 36 of the second part 18 and a through glass via 55, after processing a wet etchant. In other words, the structure of the thinned glass substrate 52 from FIG. 7 may be received from FIG. 6. The masking layer 58 may be applied on the first side 36 of the second part 18 of the thinned glass substrate 52 overlaying the damaged glass substrate region 43 but not the later obtained through glass via 55. After processing a wet etchant, the damaged glass substrate region 43 may be removed resulting in a through glass via 55 with a high aspect ratio.

According to an embodiment, the masking layer 58 at the first side 36 of the second part 18 may comprise a masking of, for example, silicon nitride, a high thermal stability material for coupling a later added metallization structure 28 on the surface of the masking layer 58 facing the first side 36 of the second part 18. The masking layer 58 material on the first side 36 of the second part 18 may be resistant to the wet etching. Because of that resistance, the wet etching provides the through glass via 55 on the first side 36 of the second part 18 of the thinned glass substrate 52. The through glass via 55 may comprise a conductive structure inside the through glass via providing an electrical connection from the first side 36 to the second side 37 of the second part 18.

FIG. 8 shows a schematic cross sectional view of the thinned glass substrate 52 and the through glass via 55 in which the through glass via 55 provides an electrical connection from the first side 36 to the second side 37 of the second part 18. The through glass via 55 may comprise a conductive structure connecting the first side 36 to the second side 37 with a conductive material, e.g., silver, copper, gold, aluminum, nickel, iron, platinum or gallium.

In other words, the conductive structure may form an electrical connection from the first side 36 to the second side 37 of the second part 18 of the thinned glass substrate 52 through the through glass via 55.

According to an embodiment, the conductive structure may comprise the same material when compared to the connection material and/or the metallization structure 28 material. In addition, FIG. 8 shows a metallization structure 28 arranged on the masking layer 58 facing the first side 36 of the second part 18 such as the metallization structure 28 already shown in FIG. 2, FIG. 6 and FIG. 7. The masking layer 58 arranged between the thinned glass substrate 52 and the metallization structure 28 may directly couple the thinned glass substrate 52 and the metallization structure 28. The metallization structures 28, one on the first side 36 and one on the second side 37 of the second part 18 may provide the electrical conductivity through the second part 18 of the thinned glass substrate 52.

Figure 9:
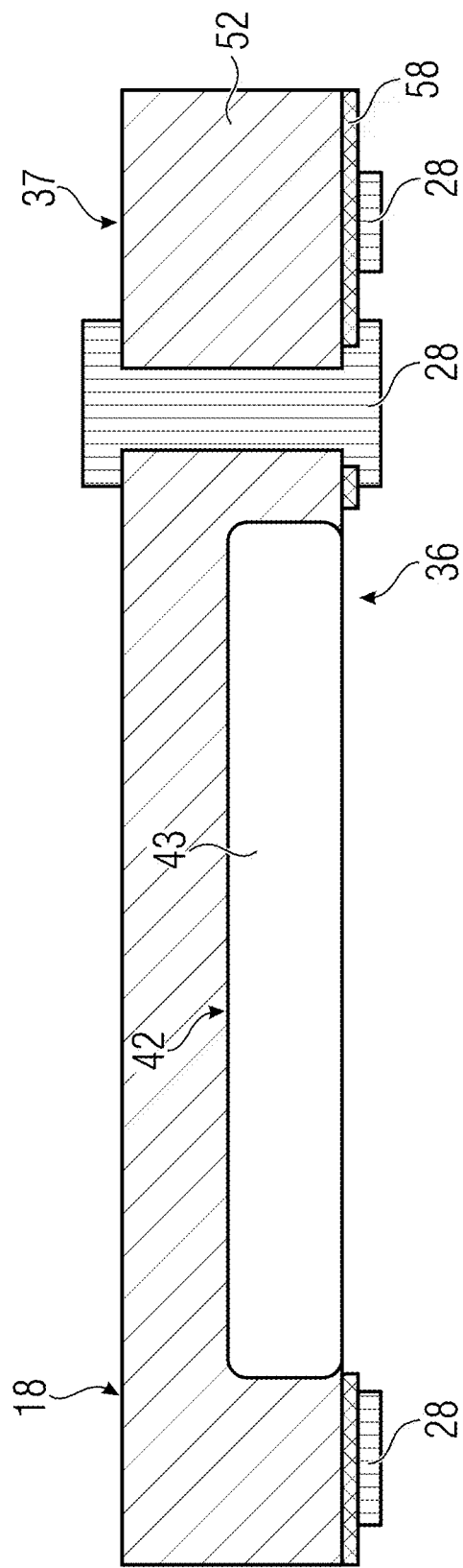
FIG. 9 shows a schematic cross-sectional view of a glass layer with an open masking layer.

FIG. 9 shows a schematic cross sectional view of the thinned glass substrate 52 in which the masking layer 58 may has an opened region on the first side 36 of the second part 18 exposing the damaged glass substrate region 43 for the later wet etching process. The opened region on the first side 36 of the second part 18 exposing the damaged glass substrate region 43 may expose at least a part or the glass substrate 32. In a later process the wet etching process may be applied on the thinned glass substrate 52 resulting in a recess 53.

Figure 10:
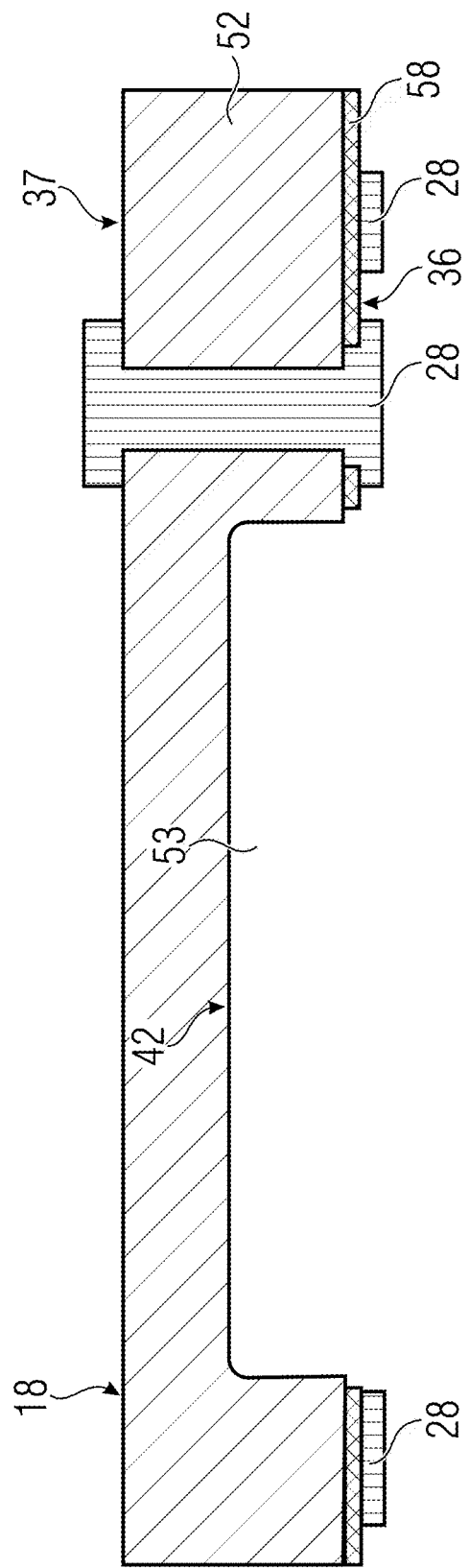
FIG. 10 shows a schematic cross-sectional view of a glass layer with a recess.

FIG. 10 shows a schematic view of the second part 18 comprising a thinned glass substrate 52, a recess 53 enclosing the cavity 14, a metallization structure 28, a through glass via as an electrical through-connection from the first side 36 to the second side 37 of the second part 18 and a masking layer 58 with a metallization structure 28 on the first side 36 of the second part 18. In other words, the structure of the thinned glass substrate 52 in FIG. 10 can be obtained by a wet etching process on the thinned glass substrate 52 in FIG. 9. In conclusion, the glass substrate is thinned, has metallization on the first 36 and second side 37 of the second part 18, a masking on the first side 36, a through glass via 55 with metallization to link the first 36 and the second side 37 of the glass substrate and a recess 53.

Figure 11:
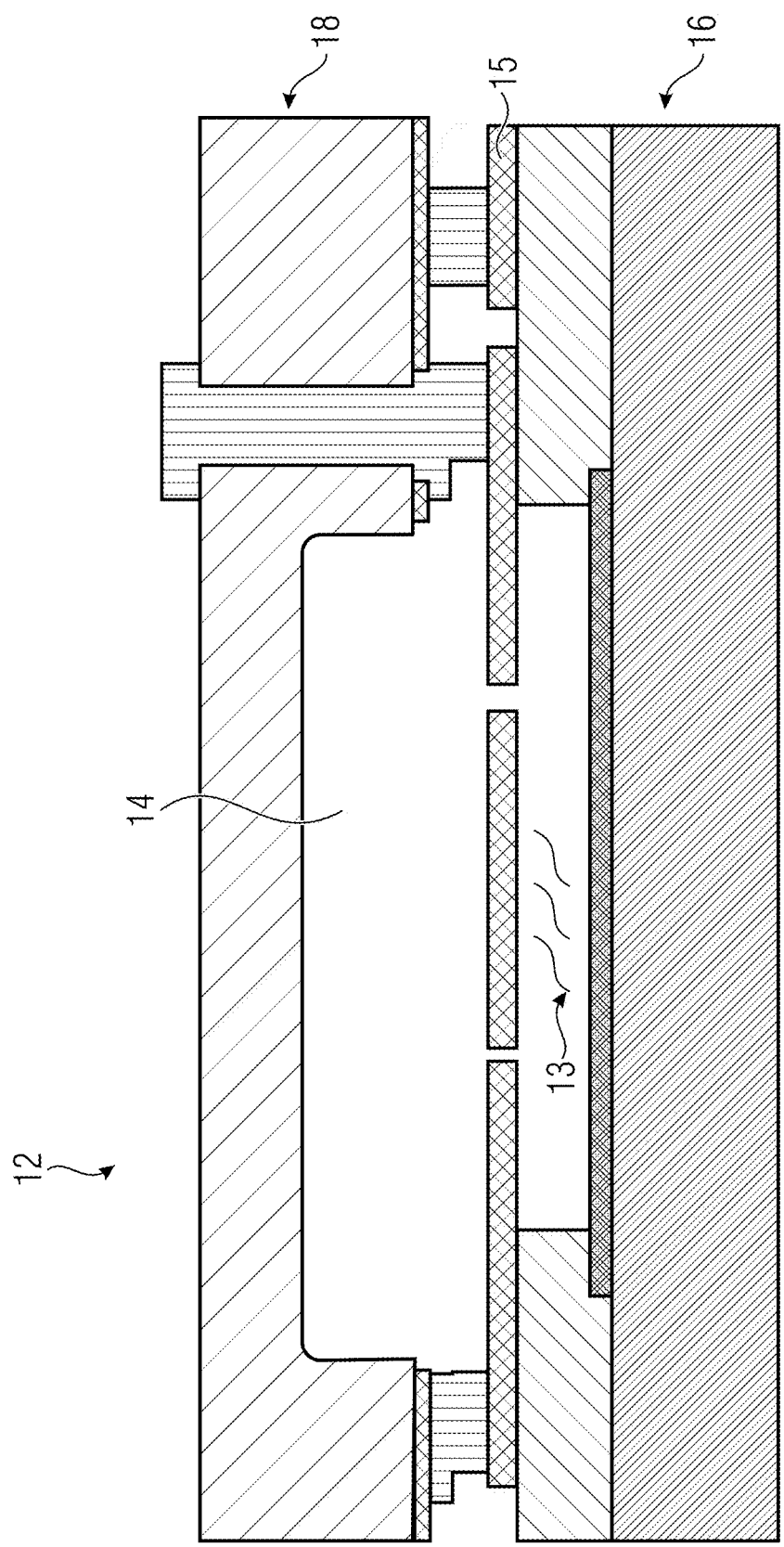
FIG. 11 shows a schematic cross-sectional view of a hermetic sealed wafer bond package.

FIG. 11 shows a schematic cross-sectional view of the package 12 with the first part 16 of the package 12 and the second part 18 of the package 12 forming a package 12 that may seal the cavity 14 hermetically. The first part 16 and the second part 18 may be bonded to each other, for example, during a wafer bonding process. For example, a metal-to-metal bond between the first part 16 and the second part 18 may be a result of the wafer bonding process. The wafer bond package may comprise a directly overlapped stack of the metallization structures 28 bonding the first part 16 and the second part 18 of the package 12. During the wafer bonding process, the metallization 28 of the first part 16 and the metallization 28 of the second part 18 may form a tight mechanical and optionally electrical connection and thus part of the hermetic sealing. Thus, the cavity 14 may be hermetically sealed so as to maintain the enclosed environment and to prevent intrusion of dust, oxygen, moisture, humidity or any outside contaminant to enter a sealed environment ensuring a corrosion-free functionality over time.

Additionally, the power consumption of the emitter 10 may be less with a hermetical sealing. Sealing the enclosure hermetically may allow to obtain a long-term stability of the generated radiation. Hermetical sealing may reduce the heat generated in the heating structure 15, may increases the allowable current of the heating structure 15 in comparison with conventional enclosures while maintaining a low power consumption, and stabilizes an output of the emitter 10. Conventional enclosures may have high electrical resistance compared to hermetically sealed enclosures. This high resistance may cause insignificant problems because of the small amount of the heat generated by the current flowing the resistance. For example, the current has to be increased in order to maintain functionality over time resulting in an increasing power consumption. More specifically, the increased current not only increases the power consumption but also increases the temperature rise in the heating structure 15 to the extent that it cannot be neglected. This temperature rise in turn may increases the resistance.

According to an embodiment, the second part 18 of the package 12 may comprise a glass substrate 32 with a recess 53 on a first side 36 of the second part 18. According to an embodiment, the pressure inside the cavity 14 is lower, for example, reduced, then the pressure outward or outside the cavity 14. According to an embodiment the emitter 10 and filter function is monolithically integrated on the same wafer. A glass lid with a pocket and a through glass via 55 is realized with a damage free process with high aspect ratio structures. Lit to infrared emitter 10 bond can be performed by metal to metal bond on wafer level within reduced gas pressure or for example, vacuum hermetically. With this layout, it shows how to minimize the complete emitter 10 and filter system in size and power consumption because of the hermetic ceiling with vacuum, for example. The size such as the height and the power consumption are both key enablers for the integration into mobile devices. The integration of IR emitters and IR filters may be monolithic.

According to an embodiment, different system concepts for a photoacoustic gas sensors are under discussion, e.g., evaluation. The infrared emitter 10 chip is realized as a MEMS chip with a thin heater membrane, a cavity 14 in a silicon substrate and optionally, at least one ventilation hole 27. The filter chip is realized as a Bragg reflector with different poly/oxide layers on a silicon substrate. An integration stacking a chip by chip on chip level may be planned with a distance holder or a standoff there. With this realization, the height of the system emitter 10 and filter system is quite high and is too high for a solution for a mobile and also shows a quite how power consumption. Therefore, this disclosure could be realized with lower MEMS system costs, lower height and size and lower power consumption. Embodiments allow a solution how to produce the complete IR emitter 10 filter package 12 with new available glass processes in a way, that the costs decrease compared to nowadays. Also the power consumption is shown to decrease due to hermetic sealing with vacuum or reduced gas pressure due to first research findings.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

The above described embodiments are merely illustrative for the principles of the present invention. It is understood that modifications and variations of the arrangements and the details described herein will be apparent to others skilled in the aft. It is the intent, therefore, to be limited only by the scope of the impending patent claims and not by the specific details presented by way of description and explanation of the embodiments herein.

What is claimed is:

1. An emitter comprising:
    a package enclosing a cavity, wherein a first part of the package is transparent for infrared radiation, and a second part of the package comprises a glass material;
    a heating structure configured for emitting the infrared radiation, wherein the heating structure is arranged in the cavity between the first part of the package and the second part of the package; and
    a filter structure configured to selectively transmit thermal radiation of a predetermined wavelength range, the heating structure arranged between the filter structure and the second part.

2. The emitter of claim 1, wherein the first part of the package comprises a semiconductor substrate.

3. The emitter of claim 1, wherein the first part of the package is transparent for the predetermined wavelength range in a first amount, and wherein the second part is transparent for the predetermined wavelength in a second amount being lower when compared to the first amount.

4. The emitter of claim 2, wherein the filter structure is arranged on a surface of the semiconductor substrate.

5. The emitter of claim 1, wherein the filter structure comprises a stack having a plurality of layers comprising a periodic variation of at least one layer characteristic.

6. The emitter of claim 1, wherein the emitter comprises a MEMS.

7. The emitter of claim 1, wherein the heating structure comprises a membrane structure.

8. The emitter of claim 1, wherein the cavity is hermetically sealed.

9. The emitter of claim 1, wherein a pressure inside of the cavity is lower than outward the cavity.

10. The emitter of claim 1, wherein the second part of the package comprises a recess on a first side of the second part.

11. The emitter of claim 1, comprising a masking layer at a first side of the second part of the package and comprising a connection layer arranged at the masking layer, the connection layer forming a mechanical connection to the first part of the package.

12. The emitter claim 11, wherein the second part of the package comprises a through glass via further comprising a same material as the connection layer.

13. A method for manufacturing an emitter, the method comprising:
    providing a heating structure;
    providing a first part of a package being transparent for infrared radiation, and a second part of the package comprising a glass material; and providing a filter structure configured to selectively transmit thermal radiation of a predetermined wavelength range, the heating structure arranged between the filter structure and the second part,
wherein the heating structure is arranged in a cavity enclosed by the package between the first part of the package and the second part of the package, and wherein the heating structure is configured for emitting the infrared radiation.

14. The method of claim 13, further comprising:
providing a masking layer at a first side of the second part of the package, the masking layer including a connection layer arranged at the masking layer, the connection layer forming a mechanical connection to the first part of the package.

15. An emitter comprising:
a package enclosing a cavity, wherein a first part of the package is transparent for infrared radiation, and a second part of the package comprises a glass material; and
a heating structure configured for emitting the infrared radiation, wherein the heating structure is arranged in the cavity between the first part of the package and the second part of the package; and
a masking layer at a first side of the second part of the package, the masking layer further comprising a connection layer arranged at the masking layer, the connection layer forming a mechanical connection to the first part of the package.

16. The emitter of claim 15, further comprising a filter structure configured to selectively transmit infrared radiation of a predetermined wavelength range, the heating structure located between the filter structure and the second part.

17. The emitter of claim 16, wherein the first part of the package has first transparency for the predetermined wavelength range, and wherein the second part has second transparency for the predetermined wavelength range wherein the second transparency is lower than the first transparency.

18. The emitter of claim 15, wherein the second part of the package comprises a through glass via further comprising a same material as the connection layer.

19. The emitter of claim 15, wherein the emitter comprises a MEMS.

20. The emitter of claim 15, wherein the heating structure comprises a membrane structure.

\* \* \* \* \*